(12) United States Patent
Qian et al.

(10) Patent No.: US 11,099,384 B2
(45) Date of Patent: Aug. 24, 2021

(54) ADJUSTING DISPLAY SETTINGS OF A HEAD-MOUNTED DISPLAY

(71) Applicant: LENOVO (Singapore) PTE. LTD., New Tech Park (SG)

(72) Inventors: Ming Qian, Cary, NC (US); Joseph Vincent Nasti, Chicago, IL (US); David Alexander Schwarz, Morrisville, NC (US); Song Wang, Cary, NC (US)

(73) Assignee: Lenovo (Singapore) PTE. LTD., New Tech Park (SG)

( * ) Notice: Subject to any disclaimer, the term of this patent is extended or adjusted under 35 U.S.C. 154(b) by 135 days.

(21) Appl. No.: 16/367,197

(22) Filed: Mar. 27, 2019

(65) Prior Publication Data

US 2020/0310117 A1 Oct. 1, 2020

(51) Int. Cl.
*G02B 27/01* (2006.01)
*A61B 5/00* (2006.01)

(52) U.S. Cl.
CPC .......... *G02B 27/017* (2013.01); *A61B 5/4076* (2013.01)

(58) Field of Classification Search
CPC combination set(s) only.
See application file for complete search history.

(56) References Cited

U.S. PATENT DOCUMENTS

| | | | |
|---|---|---|---|
| 2010/0185113 A1* | 7/2010 | Peot | A61B 5/04842 600/544 |
| 2015/0338915 A1* | 11/2015 | Publicover | H04N 5/44504 345/633 |
| 2016/0007918 A1* | 1/2016 | Badower | A61B 5/6803 600/383 |
| 2016/0345060 A1* | 11/2016 | Marci | G06K 9/00221 |
| 2017/0039045 A1* | 2/2017 | Abrahami | A61B 5/1118 |
| 2017/0135640 A1* | 5/2017 | Gunasekar | A61B 5/6843 |

OTHER PUBLICATIONS

B. Bauman et al., Visual Interface Evaluation for Wearables Datasets: Predicting the Subjective Augmented Vision Image QoE and QoS, Future Internet, Jul. 2017, pp. 1-13.

* cited by examiner

*Primary Examiner* — Shaheda A Abdin
(74) *Attorney, Agent, or Firm* — Kunzler Bean & Adamson (57) ABSTRACT

Apparatuses, methods, systems, and program products are disclosed for adjusting display settings of a head-mounted display. An apparatus includes a processor and a memory that stores code executable by the processor. The code is executable by the processor to receive sensor data from one or more sensors operably connected to a head mounted display ("HMD") unit while a user wears the HMD unit. The code is executable by the processor to determine a user's cognition level based on the sensor data. The code is executable by the processor to adjust one or more display settings of the HMD unit based on the determined cognition level for the user.

16 Claims, 7 Drawing Sheets

ADJUSTING DISPLAY SETTINGS OF A HEAD-MOUNTED DISPLAY

FIELD

The subject matter disclosed herein relates to head-mounted displays and more particularly relates to adjusting the display of head-mounted displays based on a user's cognition level.

BACKGROUND

Displays for head-mounted displays may have various settings that a user can manually adjust, similar to a display for a smart phone or a television. However, the user's ability to focus and pay attention to the display may change over time as the user wears the head-mounted display. It can be inconvenient and burdensome for the user to constantly change display settings, if they are changed at all.

BRIEF SUMMARY

An apparatus for adjusting display settings of a head-mounted display is disclosed. A system and method also perform the functions of the apparatus. In one embodiment, an apparatus includes a processor and a memory that stores code executable by the processor. In certain embodiments, the code is executable by the processor to receive sensor data from one or more sensors operably connected to a head mounted display ("HMD") unit while a user wears the HMD unit. The code, in some embodiments, is executable by the processor to determine a user's cognition level based on the sensor data. In various embodiments, the code is executable by the processor to adjust one or more display settings of the HMD unit based on the determined cognition level for the user.

In one embodiment, a system for adjusting display settings of a head-mounted display includes a head-mounted display ("HMD") unit comprising a processor and a memory that stores code executable by the processor, a headband coupled to the HMD unit, and one or more sensors coupled to the headband and operably connected to the HMD unit. In certain embodiments, the code is executable by the processor to receive sensor data from one or more sensors operably connected to a head mounted display ("HMD") unit while a user wears the HMD unit. The code, in some embodiments, is executable by the processor to determine a user's cognition level based on the sensor data. In various embodiments, the code is executable by the processor to adjust one or more display settings of the HMD unit based on the determined cognition level for the user.

In one embodiment, a method for adjusting display settings of a head-mounted display includes receiving, by a processor, sensor data from one or more sensors operably connected to a head mounted display ("HMD") unit while a user wears the HMD unit. The method, in further embodiments, includes determining a user's cognition level based on the sensor data. The method, in various embodiments, includes adjusting one or more display settings of the HMD unit based on the determined cognition level for the user.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

As will be appreciated by one skilled in the art, aspects of the embodiments may be embodied as a system, method or program product. Accordingly, embodiments may take the form of an entirely hardware embodiment or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. This code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

An apparatus for adjusting display settings of a head-mounted display is disclosed. A system and method also perform the functions of the apparatus. In one embodiment, an apparatus includes a processor and a memory that stores code executable by the processor. In certain embodiments, the code is executable by the processor to receive sensor data from one or more sensors operably connected to a head mounted display ("HMD") unit while a user wears the HMD unit. The code, in some embodiments, is executable by the processor to determine a user's cognition level based on the sensor data. In various embodiments, the code is executable by the processor to adjust one or more display settings of the HMD unit based on the determined cognition level for the user.

In one embodiment, the sensor data is sensed from one or more locations on the user's head. The one or more sensors may be coupled to a headband that is connected to the HMD unit. In further embodiments, the sensor data comprises electroencephalography ("EEG") data sensed from the one or more locations on the user's head.

In one embodiment, the EEG data comprises a measurement of a signal strength that the one or more sensors sense within the beta-wave range. The user's cognition level may be determined according to the measured signal strength. In certain embodiments, the one or more sensors comprise one or more electrode probes and the one or more locations on the user's head where the sensors are located is selected from the group consisting of FP1, FP2, TP9, and TP10 locations.

In various embodiments, the code is further executable by the processor to monitor, over time, the user's cognition level based on new sensor data from the one or more sensors while the user wears the HMD unit and further adjust the one or more display settings of the HMD unit based on the user's cognition level. In some embodiments, the code is further executable by the processor to notify the user that the one or more sensors are not positioned in a correct location on the user's head in response to not receiving sensor data from one or more of the sensors.

In one embodiment, the code is further executable by the processor to generate a baseline of sensor data for a period of time after the HMD unit is activated prior to determining the user's cognition level and adjusting the one or more display settings of the HMD unit. In certain embodiments, the code is further executable by the processor to acquire biometric data for the user to further determine the user's cognition level.

In one embodiment, the biometric data is selected from the group consisting of a skin conductivity for the user, a heart rate for the user, a blood pressure for the user, and an oxygen level for the user. In some embodiments, the code is executable by the processor to present one or more of an augmented reality ("AR") environment and a virtual reality ("VR") environment on a display of the HMD unit.

In one embodiment, adjusting one or more settings of the HMD unit includes changing one or more settings of the VR and AR environment. The one or more settings may be selected from the group consisting of a brightness setting of elements presented on the display, a contrast setting of the display between elements presented on the display and an actual background, a color of elements presented on the display, and a size of elements presented on the display.

In one embodiment, a system for adjusting display settings of a head-mounted display includes a head-mounted display ("HMD") unit comprising a processor and a memory that stores code executable by the processor, a headband coupled to the HMD unit, and one or more sensors coupled to the headband and operably connected to the HMD unit. In certain embodiments, the code is executable by the processor to receive sensor data from one or more sensors operably connected to a head mounted display ("HMD") unit while a user wears the HMD unit. The code, in some embodiments, is executable by the processor to determine a user's cognition level based on the sensor data. In various embodiments, the code is executable by the processor to adjust one or more display settings of the HMD unit based on the determined cognition level for the user.

In one embodiment, the one or more sensors comprise one or more electrode probes positioned at one or more locations on the user's head. The one or more locations may be selected from the group consisting of TP9, FP1, FP2 and TP10 locations. In some embodiments, the sensor data comprises electroencephalography ("EEG") data sensed from the one or more electrode probes located on the user's head.

In one embodiment, the code is executable by the processor to present one or more of an augmented reality ("AR") environment and a virtual reality ("VR") environment on a display of the HMD unit. The one or more settings of the VR and AR environment that are adjusted may be selected from the group consisting of a brightness setting of elements presented on the display, a contrast setting of the display between elements presented on the display and an actual background, a color of elements presented on the display, and a size of elements presented on the display.

In one embodiment, a method for adjusting display settings of a head-mounted display includes receiving, by a processor, sensor data from one or more sensors operably connected to a head mounted display ("HMD") unit while a user wears the HMD unit. The method, in further embodiments, includes determining a user's cognition level based on the sensor data. The method, in various embodiments, includes adjusting one or more display settings of the HMD unit based on the determined cognition level for the user.

In one embodiment, the method includes monitoring, over time, the user's cognition level based on new sensor data from the one or more sensors while the user wears the HMD unit and further adjusting the one or more display settings of the HMD unit based on the user's cognition level.

In certain embodiments, the method includes notifying the user that the one or more sensors are not positioned in a correct location on the user's head in response to not receiving sensor data from one or more of the sensors. In one embodiment, the method includes generating a baseline of sensor data for a period of time after the HMD unit is activated prior to determining the user's cognition level and adjusting the one or more display settings of the HMD unit.

Figure 1A:
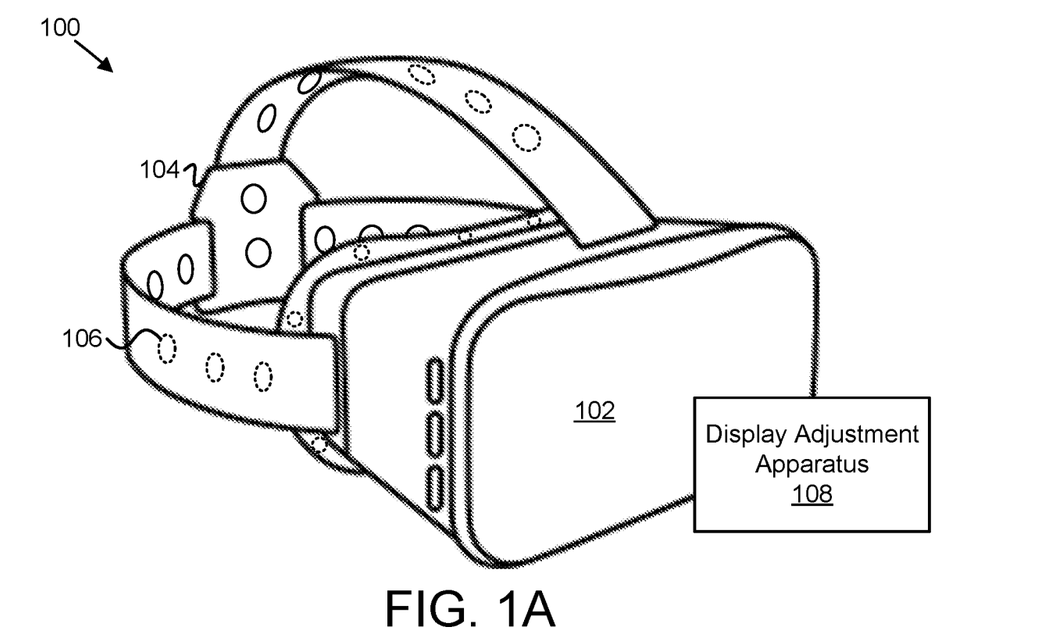
FIG. 1A is a schematic block diagram illustrating one embodiment of a system for adjusting display settings of a head-mounted display.

FIG. 1 is a schematic block diagram illustrating one embodiment of a system 100 for adjusting display settings of a head-mounted display. In one embodiment, the system 100 includes a head mounted display ("HMD") unit 102. As used herein, an HMD unit 102 may refer to a display device that is worn on a user's head and has a display positioned in front of the user's eyes. A typical HMD unit 102 has one or two small displays, with lenses and semi-transparent mirrors embedded in eyeglasses (also termed data glasses), a visor, or a helmet. An HMD unit 102 may have one or two (or more) small displays, with lenses and semi-transparent mirrors embedded in eyeglasses (also termed data glasses), a visor, or a helmet. The displays may be miniaturized and may include cathode ray tubes ("CRT"), liquid crystal displays ("LCDs"), liquid crystal on silicon ("LCos"), or organic light-emitting diodes ("OLED").

In certain embodiments, the HMD unit 102 may be configured to mount, hold, or otherwise couple to a smart phone, which becomes the computing device and display for the HMD unit 102. In such an embodiment, the smart phone, or other mobile device, may be operably coupled to the HMD unit 102 to enable a user to interact with the smart phone, receive data from the HMD unit 102, turn on/off using controls on the HMD unit 102, and/or the like. Otherwise, the display and computing device is integrated into the HMD unit 102 to form a single unit. The computing device may comprise various processors or processor cores, memory, storage, network connectivity chips, graphics chips, audio chips, and/or the like.

The HMD unit 102 may be configured to present a virtual reality or augmented reality environment. As used herein, a virtual reality ("VR") environment is an interactive, virtual, digital, or otherwise computer generated three-dimensional environment or simulation. An augmented reality ("AR") environment may be considered a form of virtual reality that layers virtual information over a camera feed into an HMD unit 102 or through a smartphone or tablet or other device coupled to the HMD unit 102 giving the user the ability to view three-dimensional images.

In one embodiment, the HMD unit 102 is coupled to a headband 104 that is configured to go over/around the user's head and hold the HMD unit 102 against the user's eyes/face. As shown in FIG. 1, the headband 104 may encompass the user's head using different bands. In certain embodiments, a single headband 104 that goes around the user's head may be used, or other bands that go over the user's head may be used to add additional support for the HMD unit 102. Other embodiments may include arms, similar to arms for eyeglasses, that sit on the user's ears, a chin strap for securing the HMD unit 102 to the user's head, a helmet that totally encloses the user's head, a visor, and/or the like.

In one embodiment, the headband 104 includes one or more sensors 106 that are used to sense, collect, detect, and/or the like information from different locations on the user's head such as the user's scalp, forehead, face, ears, neck, and/or the like. In certain embodiments, the sensors 106 comprise electrode probes that are communicatively and/or operatively coupled to the HMD display 102 via electrical lines, cables, wires, or the like that are embedded in the headband 104. For instance, the HMD unit 102 may comprise a signal generator or other power source that is used to activate the electrode probes, and the electrode probes may send signals, data, information, or the like that is sensed from the user's head to the HMD unit 102. The electrode probes may comprise "dry" probes that do not require a gel or other viscous agent to be applied to the user's head to sense, detect, or capture a signal from the user's head.

In certain embodiments, the electrodes are used to capture electroencephalography ("EEG") data sensed from one or more locations on the user's head. As used herein, EEG may refer to an electrophysiological monitoring method to record electrical activity of the brain. As shown in the electrode map 120 illustrated in FIG. 1B, electrode probes may be placed at predefined locations 120 on the user's head 122 depending on the parts of the brain that are of interest to measure.

Figure 1B:
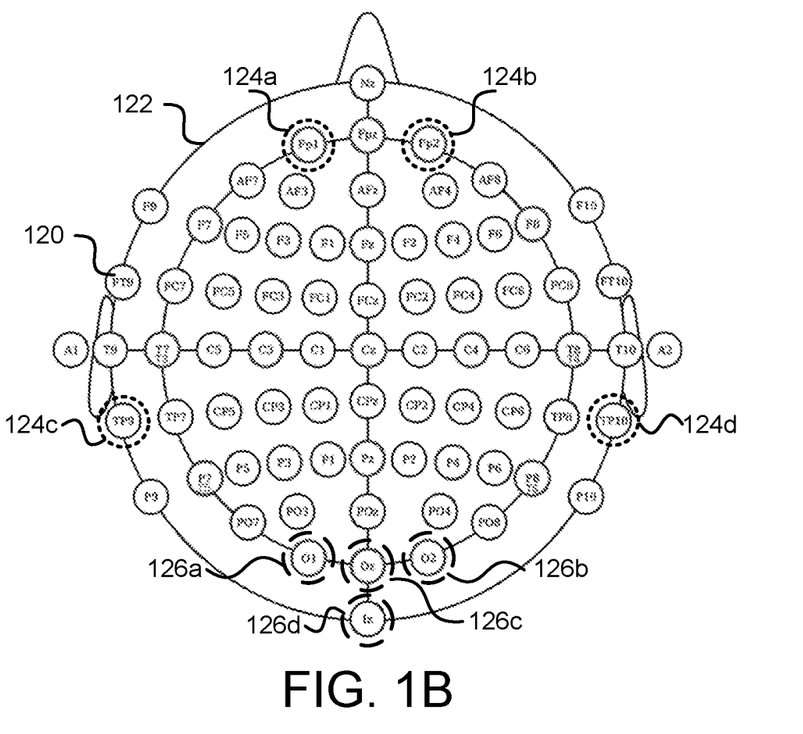
FIG. 1B is a schematic block diagram illustrating one embodiment of a map of electrode placement on a user's head.

For instance, in one embodiment described below, the electrode probes may be placed in the headband 104 such that the electrode probes are positioned over locations FP1 124a, FP2 124b, TP9 124c, and TP10 124d (collectively 124) on the user's head 122 (scalp) to measure the cognition level of the user. As used herein, a user's cognition level may refer to the user's current ability to process data, acquire knowledge, perceive surroundings, maintain attention, or the like. In other words, the user's cognition may encompass may aspects of intellectual functions and processes such as attention, the formation of knowledge, memory and working memory, judgment and evaluation, reasoning and "computation", problem solving and decision making, comprehension and production of language.

Similarly, the electrode probes may be placed in the headband 104 such that the electrode probes are positioned over locations O1 126a, O2 126b, Oz 126c, and Iz 126d (e.g., the back of the head) (collectively 124) on the user's head 122 (scalp) to measure the visual acuity of the user. As used herein, visual acuity may refer to the clarity of the user's vision, which may be detected, estimated, determined, or the like based on measuring brain activity using electrode probes at the foregoing locations on the user's head 122.

In one embodiment, the display adjustment apparatus 108 is configured to determine the user's cognitive level and/or the user's visual acuity based on the data that is sensed using the one or more sensors 106 that are located on the user's head 122, and dynamically adjust one or more display settings for the HMD unit 102 to enhance or reduce the user's cognitive level, correct or enhance the user's visual acuity, and/or the like, as described in more detail below. For instance, the display adjustment apparatus 108 may automatically adjust the display of various augment reality overlay elements to help the user focus or to draw the user's focus on to display. In various embodiments, the display adjustment apparatus 108 may be embodied as a hardware appliance that can be installed or deployed on/in an HMD unit 102.

The display adjustment apparatus 108, in such an embodiment, may include a semiconductor integrated circuit device (e.g., one or more chips, die, or other discrete logic hardware), or the like, such as a field-programmable gate array ("FPGA") or other programmable logic, firmware for an FPGA or other programmable logic, microcode for execution on a microcontroller, an application-specific integrated circuit ("ASIC"), a processor, a processor core, or the like. In one embodiment, the display adjustment apparatus 108 may be mounted on a printed circuit board with one or more electrical lines or connections (e.g., to volatile memory, a non-volatile storage medium, a network interface, a peripheral device, a graphical/display interface, or the like). The hardware appliance may include one or more pins, pads, or other electrical connections configured to send and receive data (e.g., in communication with one or more electrical lines of a printed circuit board or the like), and one or more hardware circuits and/or other electrical circuits configured to perform various functions of the display adjustment apparatus 108.

The semiconductor integrated circuit device or other hardware appliance of the display adjustment apparatus 108, in certain embodiments, includes and/or is communicatively coupled to one or more volatile memory media, which may include but is not limited to random access memory ("RAM"), dynamic RAM ("DRAM"), cache, or the like. In one embodiment, the semiconductor integrated circuit device or other hardware appliance of the display adjustment apparatus 108 includes and/or is communicatively coupled to one or more non-volatile memory media, which may include but is not limited to: NAND flash memory, NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon ("SONOS"), resistive RAM ("RRAM"), programmable metallization cell ("PMC"), conductive-bridging RAM ("CBRAM"), magneto-resistive RAM ("MRAM"), dynamic RAM ("DRAM"), phase change RAM ("PRAM" or "PCM"), magnetic storage media (e.g., hard disk, tape), optical storage media, or the like.

Figure 2:
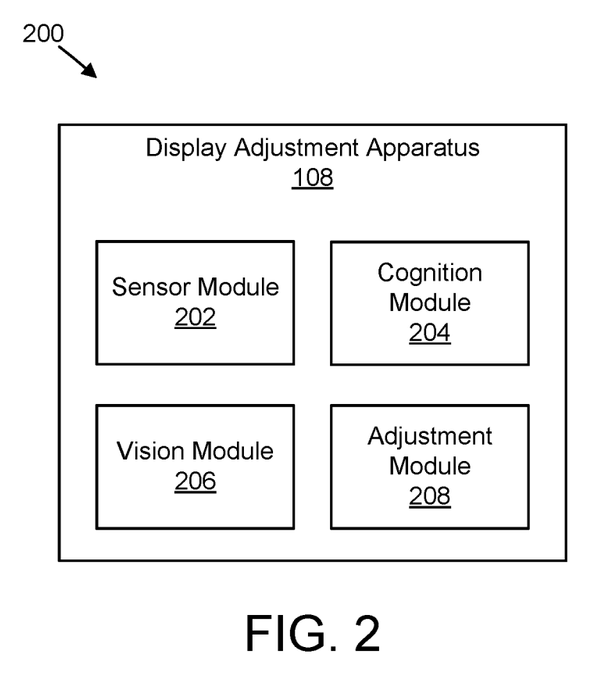
FIG. 2 is a schematic block diagram illustrating one embodiment of an apparatus for adjusting display settings of a head-mounted display.

FIG. 2 is a schematic block diagram illustrating one embodiment of an apparatus 200 for adjusting display settings of a head-mounted display. In one embodiment, the apparatus 200 includes an instance of a display adjustment apparatus 108. In certain embodiments, the display adjustment apparatus 108 includes one or more of a sensor module 202, a cognition module 204, a vision module 206, and an adjustment module 208, which are described in more detail below.

The sensor module 202, in one embodiment, is configured to receive sensor data from one or more sensors 106 operably connected to an HMD unit 102 while a user wears the HMD unit 102. As described above, the sensors 106 may comprise electrode probes that are integrated into the headband 104 that is used to wear the HMD unit 102. The sensor data, in certain embodiments, includes EEG data that describes brain activity at the various locations where the sensors 106 are located on the user's head 122.

In one embodiment, as it relates to determining the user's cognition level, the EEG data comprises a measurement or quantified value of a signal strength that the one or more sensors 106 detect or sense (e.g., that an electrode probe measures) at the predetermined locations 124 on the user's head 122 associated with cognition within the beta-wave frequency range or band, which is typically in the 12-30 Hertz range.

In further embodiments, as it relates to determining the user's visual acuity, the EEG data comprises a measurement or quantified value of a signal strength that the one or more sensors 106 detect or sense (e.g., that an electrode probe measures) at the predetermined locations 126 on the user's head 122 associated with visual acuity within the theta- and alpha-wave frequency ranges or bands, which are typically in the 4-7.5 Hertz and the 8-10 Hertz ranges, respectively.

In one embodiment, the cognition module 204 is configured to determine the user's cognition level based on the sensor data. For instance, the cognition module 204 may determine whether the beta-wave frequency data satisfies a threshold value associated with a predefined cognition level, is within a frequency range or band associated with a predefined cognition level, and/or the like. In such an embodiment, the cognition module 204 performs a time-frequency or wavelet transform on the EEG data that the sensors 106 sense, and the amplitude of the transform in the beta-band frequency range (16-31 Hertz) is measured to determine the user's cognition level over time.

In one embodiment, the threshold value may be a predefined and/or default value, a value determined based on other characteristics of the user (e.g., the user's age, weight, heart rate, blood pressure, and/or other biometric information), a value determined as the result of a survey, quiz, or other subjective information, a value determined as a result of a calibration test, and/or the like. For instance, the cognition module 204 may take initial EEG readings based on information presented on the display that is intended to activate different parts of the user's brain associated with the user's cognition level, acquire biometric data, and/or gather subjective data from a user in the form of a survey or health questions to set a benchmark, and corresponding thresholds based on the benchmark, for the user's cognition level.

For example, if the power (e.g., EEG data) that is measured and calculated in a beta-wave frequency band is too high (exceeds a power threshold calculated in the beta-wave band or is within a power threshold range calculated in the beta-wave band), e.g., between 24 and 30 Hertz, then the cognition module 204 may determine that the user is experiencing high levels of adrenaline, anxiety, arousal, inability to relax, stress, or the like, and therefore may not be able to focus on what he/she is doing because the user is too "worked up" or "excited".

Similarly, if the power that is measured and calculated in the beta-wave frequency band is too low (is less than a power threshold calculated in the beta-wave band or is within a power threshold range calculated in the beta-wave band), e.g., between 12 and 18 Hertz, then the cognition module 204 may determine that the user is experiencing fatigue, daydreaming, depression, sleepiness, boredom, or the like. Accordingly, the optimal beta-wave frequency band or range for the user may be somewhere between the lower and higher ranges, e.g., 18-24 Hertz, which may indicate that the user is able to focus, learn, retain memories, problem solve, or the like. Based on the values of the power that is measured and calculated in the beta-wave frequency band, the adjustment module 208, described below, can determine how to adjust the display settings of the HMD unit 102 to help the user focus.

In one embodiment, the vision module 206 is configured to determine the user's visual acuity based on the sensor data. For instance, the vision module 206 may determine whether the theta- and alpha-wave frequency data satisfies a threshold value associated with a predefined visual acuity, is within a frequency range or band associated with a predefined visual acuity, and/or the like. In such an embodiment, the cognition module 204 performs a time-frequency or wavelet transform on the EEG data that the sensors 106 sense, and the amplitude of the transform in the theta-band frequency range (4-7.5 Hertz) and the alpha-band frequency range (8-10 Hertz) is measured to determine the user's visual acuity over time. These two bands, the alpha- and theta-wave bands, may relate to visual cortex activity with prominent spectral power mean changes within the theta-wave 5.73-6.22 Hertz frequency range.

In one embodiment, the threshold value may be a predefined and/or default value, a value determined based on other characteristics of the user (e.g., the user's age, weight, heart rate, blood pressure, and/or other biometric information), a value determined as the result of a survey, quiz, or other subjective information, a value determined as a result of an eye-exam presented on the display, a value determined as a result of a calibration test, and/or the like. For instance, the vision module 206 may take initial EEG readings based on information presented on the display that is intended to activate different parts of the user's brain associated with the user's visual acuity, acquire biometric data, and/or gather subjective data from a user in the form of a survey or health questions to set a benchmark, and corresponding thresholds based on the benchmark, for the user's visual acuity.

For example, if the power (e.g., EEG data) that is measured and calculated in the theta-wave frequency band is too high (exceeds a power threshold calculated in the theta-wave band or is within a power threshold range calculated in the theta-wave band), e.g., around 7.5 Hertz, or too low (less than a power threshold calculated in the theta-wave band or is within a power threshold range calculated in the theta-wave band), e.g., around 4 Hertz, and/or the power that is measured and calculated in the alpha-wave frequency band is too high (exceeds a power threshold calculated in the alpha-wave band or is within a power threshold range calculated in the alpha-wave band), e.g., around 10 Hertz, or too low (is less than a power threshold calculated in the alpha-wave band or is within a power threshold range calculated in the alpha-wave band), e.g., around 8 Hertz, then the vision module 206 may determine, based on the user's brain activity, that the user's vision is impaired or the user is otherwise having a difficult time focusing his/her vision, and therefore may not be able to focus on what he/she is doing. Based on the values of the power that is measured and calculated in the theta- and alpha-wave frequency bands, the adjustment module 208, described below, can determine how to adjust the display settings of the HMD unit 102 to correct for the user's vision impairment, fatigue, or the like.

In one embodiment, the adjustment module 208 is configured to adjust one or more display settings for the HMD unit 102 based on the determined cognition level for the user. For instance, in one embodiment, adjusting one or more display settings of the HMD unit 102 may include changing one or more settings of the VR and/or AR environments to help the user achieve an optimal cognition level for focusing (e.g., to calm or relax the user or to excite or "wake up" the user). For example, the adjustment module 208 may adjust a brightness setting of AR/VR graphical elements presented on the display (to make the graphical elements brighter or dimmer), a contrast setting of the display between AR/VR graphical elements presented on the display and an actual background (to make the graphical elements stand-out more or less), a color setting of graphical elements presented on the display (to make graphical elements appear with brighter, more noticeable colors, or duller, less noticeable colors), a size of graphical elements presented on the display (to make the graphical items appear larger or smaller), and/or the like.

In one embodiment, the adjustment module 208 is configured to adjust one or more display settings for the HMD unit 102 based on the determined visual acuity for the user. For instance, in one embodiment, adjusting one or more display settings of the HMD unit 102 may include changing one or more settings of the VR and/or AR environments to correct for the user's impaired vision (e.g., to correct for blurry vision, astigmatism, near-sightedness or far-sightedness, or the like). For example, the adjustment module 208 may adjust a resolution of the display, a pixel density of the display, and/or a zoom setting of the display (to make graphical elements appear sharper, larger, smaller, or the like); a contrast setting of the display between AR/VR graphical elements presented on the display and an actual background (to make the graphical elements stand-out more or less, to make the graphical elements appear sharper or less blurry); a color setting of graphical elements presented on the display (to make graphical elements appear with brighter, more noticeable colors, or duller, less noticeable colors); a size of graphical elements presented on the display (to make the graphical items appear larger or smaller); a font size of text on the display (to make it easier to read); and/or the like.

In this manner, the display adjustment apparatus 108 can dynamically adjust various display settings of an HMD unit 102 based on detecting, reading, and interpreting brain activity of the user to assist with the user's cognition level and/or visual acuity.

Figure 3:
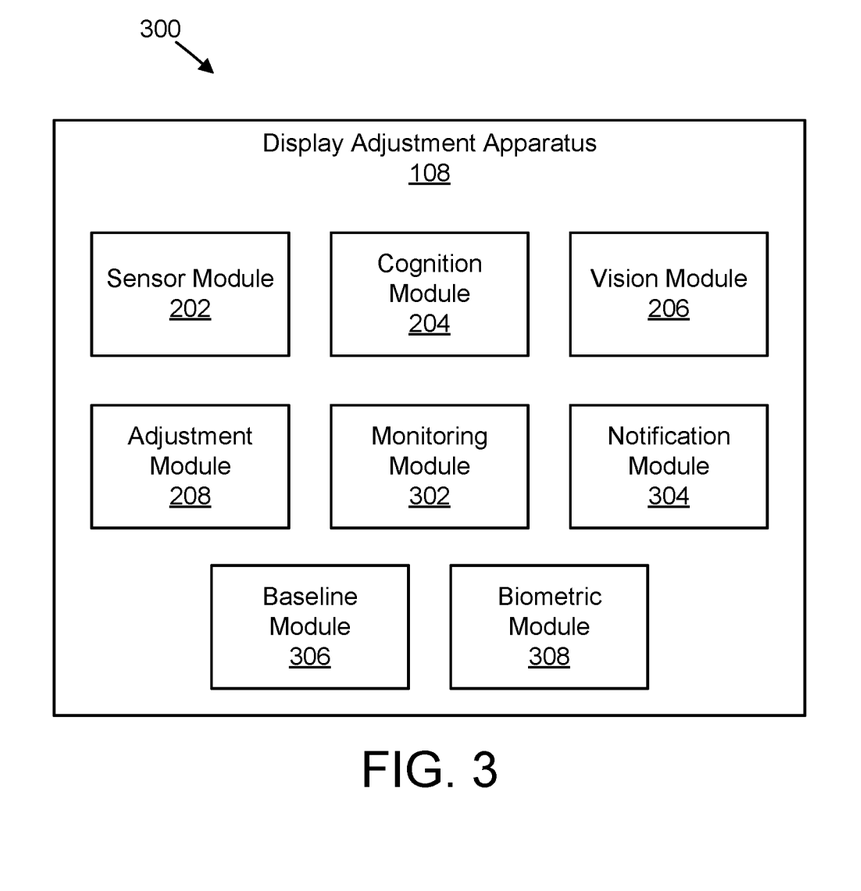
FIG. 3 is a schematic block diagram illustrating one embodiment of another apparatus for adjusting display settings of a head-mounted display.

FIG. 3 is a schematic block diagram illustrating one embodiment of another apparatus 300 for adjusting display settings of a head-mounted display. In one embodiment, the apparatus 300 includes an instance of a display adjustment apparatus 108. In certain embodiments, the display adjustment apparatus 108 includes one or more of a sensor module 202, a cognition module 204, a vision module 206, and an adjustment module 208, which may be substantially similar to the sensor module 202, the cognition module 204, the vision module 206, and the adjustment module 208 described above with reference to FIG. 2. In further embodiments, the display adjustment apparatus 108 includes one or more of a monitoring module 302, a notification module 304, a baseline module 306, and a biometric module 308, which are described in more detail below.

In one embodiment, the monitoring module 302 is configured to monitor, over time, the user's cognition level and/or visual acuity based on new sensor data from the one or more sensors 106 while the user wears the HMD unit 102. For instance, the monitoring module 302 may periodically poll, check, request, or the like sensor data from the sensors 106, e.g., every thirty seconds. In certain embodiments, the sensors 106 may be configured to sample and send sensor data on a periodic basis, e.g., every thirty seconds. Based on the new sensor data, the cognition module 204 may determine the user's current cognition level and/or the vision module 206 may determine the user's current visual acuity, and the adjustment module 208 may adjust the display settings accordingly.

In one embodiment, the notification module 304 is configured to notify the user that the one or more sensors 106 are not positioned in a correct location on the user's head 122 in response to not receiving sensor data from one or more of the sensors 106. For instance, if the notification module 304 detects that a sensor 106 is not reading or returning any EEG data, or that the sensor is returning incorrect or garbage data, the notification module 304 may display a notification on the display of the HMD unit 102, may provide an audio notification, or the like indicating that the headband 104 and/or sensors 106 need to be adjusted so that accurate data readings can be acquired.

In one embodiment, the baseline module 306 is configured to generate a baseline of sensor data for a period of time after the HMD unit 102 is activated prior to determining the user's cognition level and/or visual acuity and adjusting the one or more display settings of the HMD unit 102. In certain embodiments, the baseline module 306 may run a calibration program/application to determine whether the sensors are collecting data, are gathering reliable data, and/or to acclimate the user to the HMD unit 102. The calibration process may include an application, process, or program designed to test, activate, or the like the various areas of the brain that are associated with the user's cognition level and/or visual acuity.

Once the HMD unit 102 is up and running, and the user is running an application and workload for a period of time (e.g., five minutes, ten minutes, or the like) to give the user's brain a chance to stabilize or reach a steady state, the cognition module 204 may determine the user's cognition level and/or the vision module 206 may determine the visual acuity of the user after the baseline data set is established. Accordingly, the adjustment module 208 may adjust various display settings based on the user's cognition level or visual acuity.

In one embodiment, the biometric module 308 is configured to acquire biometric data for the user to further determine or verify the user's cognition level and/or visual acuity as determined based on the sensor data from the sensors 106 in the HMD unit 102 headband 104. The biometric data may be acquired from a wearable device such as a smart watch, a fitness band, biometric sensors on the HMD unit 102 or headband 104, and/or the like.

For instance, the biometric module 308 may use biometric data to determine a skin conductivity for the user, a heart rate for the user, a blood pressure for the user, and/or an oxygen level for the user, which may be used to verify or supplement the cognition level for the user that is determined using the sensors 106 in the headband 104. For example, if the cognition module 204 determines that the user is excited based on the beta-wave frequency EEG data, the biometric module 308 may verify this conclusion based on determining that the user has a heightened breathing rate, adrenaline level, heart rate, and/or the like.

Similarly, the biometric module 308 may use biometric data from an in- or on-ear device, e.g., a Bluetooth® headset, to determine or verify the user's visual acuity. In certain embodiments EEG or other sensors may be placed in or on the ear to sense, sample, or capture brain or head activity associated with the user's visual acuity, which may be used to supplement or verify the conclusion that the vision module 206 reaches regarding the user's visual acuity based on the theta- and alpha-wave frequency EEG data captured by the sensors 106 in the headband 104. Other biometric data may be collected that is associated with or otherwise provides an indication of the user's visual acuity such as, for example, blood pressure, heart rate, oxygen levels, adrenaline levels, breathing rate, and/or the like, which may be sensed using one or more sensors 106 of the HMD unit 102, using sensors on wearable devices such as fitness bands, smart watches, and/or the like.

Figure 4:
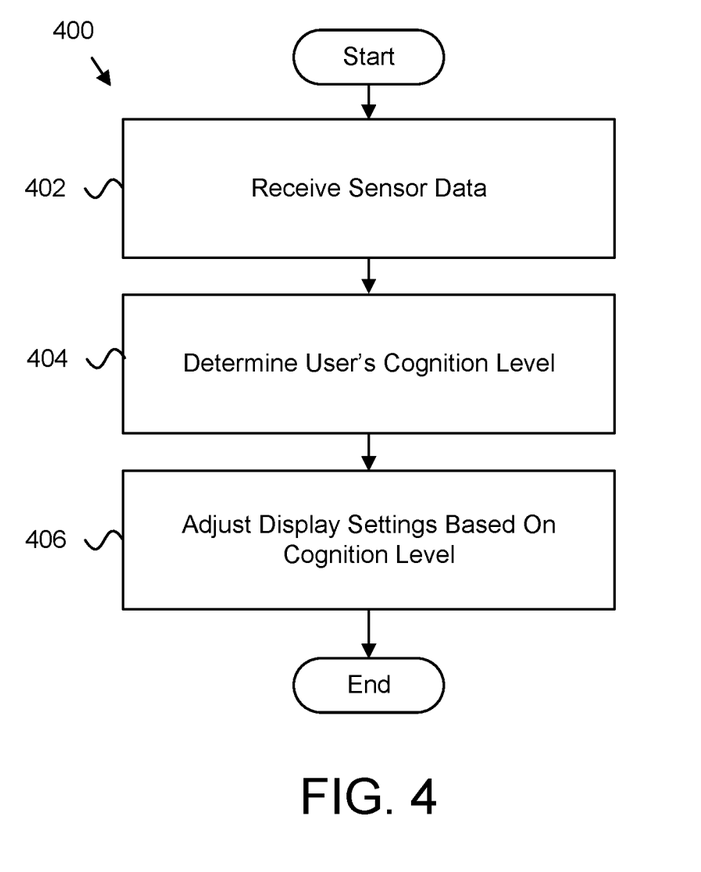
FIG. 4 is a schematic flow chart diagram illustrating one embodiment of a method for adjusting display settings of a head-mounted display.

FIG. 4 is a schematic flow chart diagram illustrating one embodiment of a method 400 for adjusting display settings of a head-mounted display. In one embodiment, the method 400 begins and receives 402 sensor data from one or more sensors 106 operably connected to an HMD unit 102 while a user wears the HMD unit 102. In some embodiments, the method 400 determines 404 a user's cognition level based on the sensor data. In further embodiments, the method 400 adjusts 406 one or more display settings of the HMD unit based on the determined cognition level for the user, and the method 400 ends. In some embodiments, the sensor module 202, the cognition module 204, and the adjustment module 208 perform the various steps of the method 400.

Figure 5:
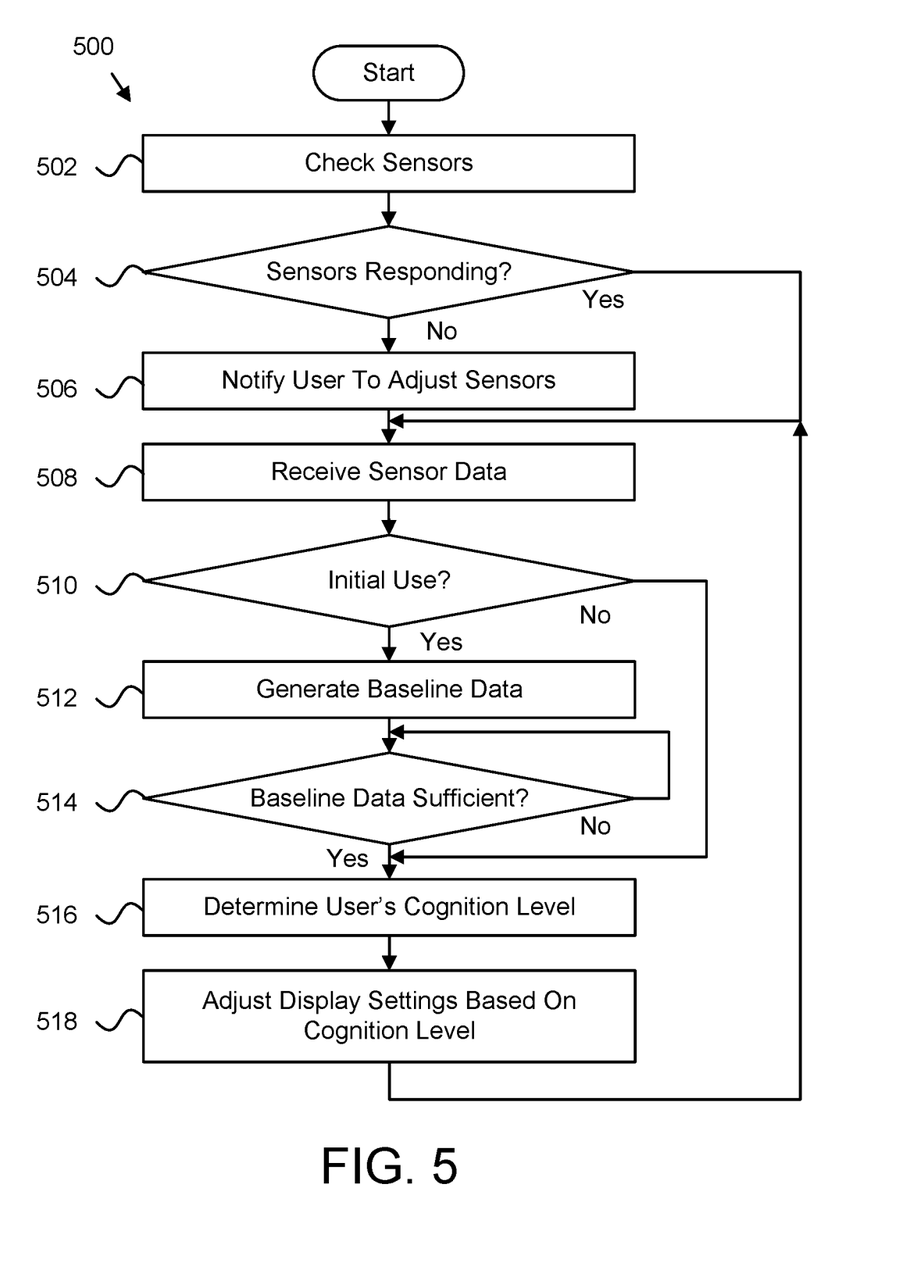
FIG. 5 is a schematic flow chart diagram illustrating one embodiment of another method for adjusting display settings of a head-mounted display.

FIG. 5 is a schematic flow chart diagram illustrating one embodiment of another method 500 for adjusting display settings of a head-mounted display. In one embodiment, the method 500 begins and checks 502 the sensors 106 to determine 504 whether the sensors 106 are responding, reading data, reading accurate data, and/or the like. If the method 500, in one embodiment, determines 504 that the sensors are not responding correctly, the method 500 notifies 506 the user to adjust the headband 104 and/or sensors 106.

In one embodiment, the method 500 receives 508 sensor data from the sensors 106 while the user wears the HMD unit 102. The method 500 may determine 510 whether this is the first time that the user has worn the HMD unit 102, if the user just activated the HMD unit 102, or the like. If so, then the method 500, in certain embodiments, generates 512 a baseline of sensor data for a period of time after the HMD unit 102 is activated prior to determining the user's cognition level and adjusting the one or more display settings of the HMD unit 102.

If the method 500, in certain embodiments, determines 514 that the baseline data is sufficient, e.g., after a period of time, after the workload running on the HMD unit 102 and/or the sensor data has reached a steady state, after completing a calibration process, or the like, the method 500 determines 516 the user's cognition level based on the sensor data, e.g., based on the beta-wave frequency data and adjusts 518 the display settings of the HMD unit 102 accordingly. The method 500, in certain embodiments, continues to receive 508 sensor data, monitor the user's cognition level, and adjust the display settings of the HMD unit 102. In some embodiments, the sensor module 202, the cognition module 204, the adjustment module 208, the monitoring module 302, the notification module 304, and the baseline module 306 perform the various steps of the method 500.

Figure 6:
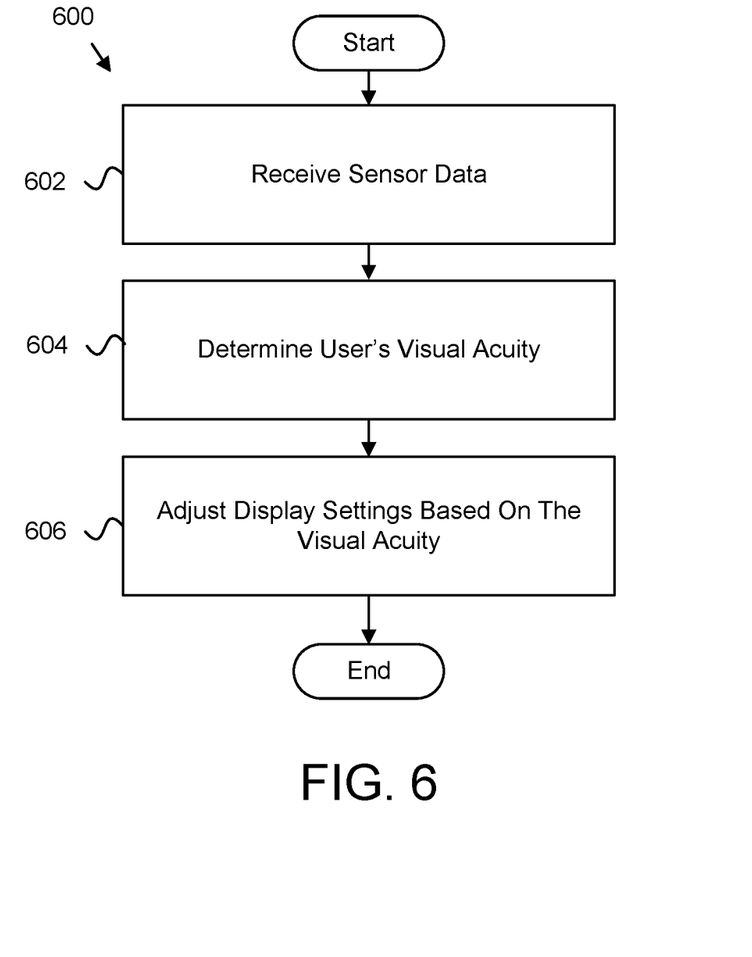
FIG. 6 is a schematic flow chart diagram illustrating one embodiment of a further method for adjusting display settings of a head-mounted display.

FIG. 6 is a schematic flow chart diagram illustrating one embodiment of a method 600 for adjusting display settings of a head-mounted display. In one embodiment, the method 600 begins and receives 602 sensor data from one or more sensors 106 operably connected to an HMD unit 102 while a user wears the HMD unit 102. In some embodiments, the method 600 determines 604 a user's visual acuity based on the sensor data. In further embodiments, the method 600 adjusts 606 one or more display settings of the HMD unit based on the determined visual acuity for the user to correct impairments in the user's visual acuity, and the method 600 ends. In some embodiments, the sensor module 202, the vision module 206, and the adjustment module 208 perform the various steps of the method 600.

Figure 7:
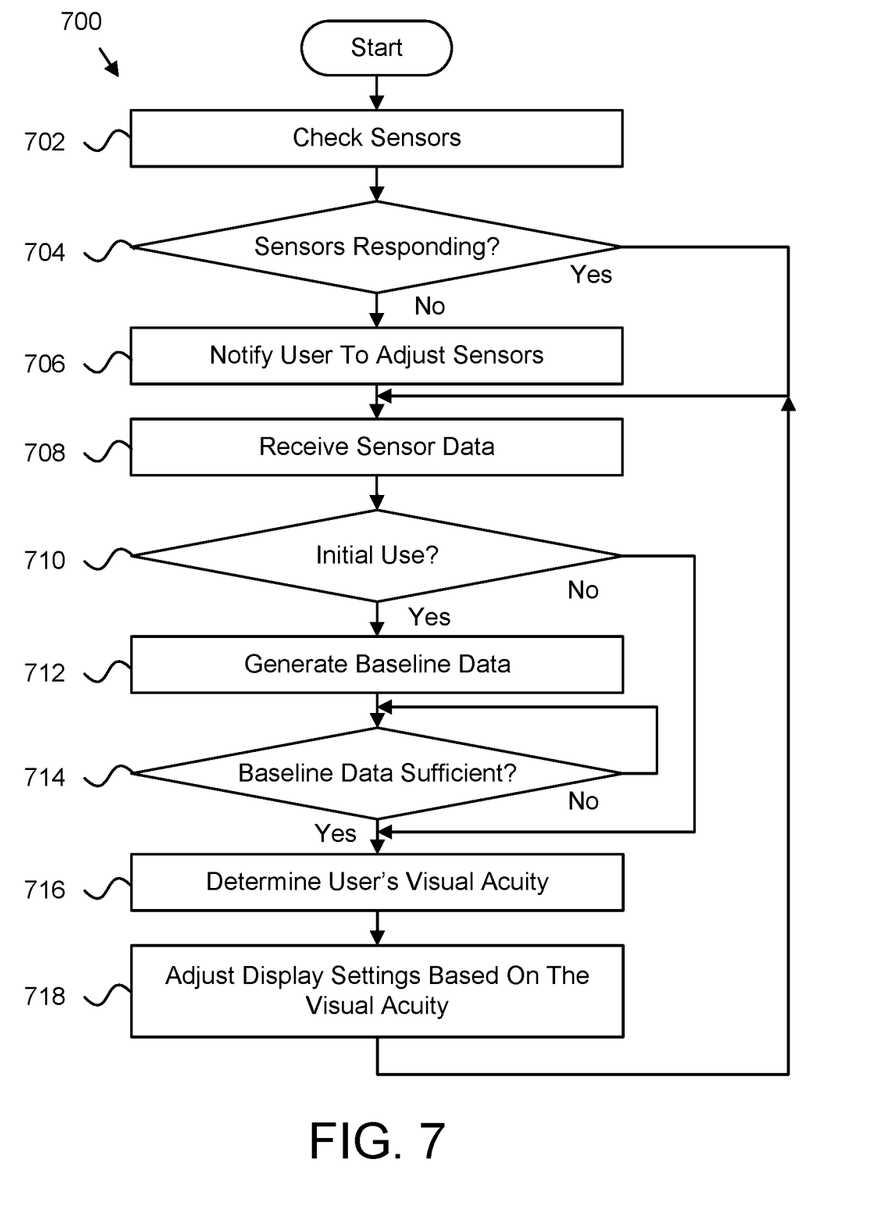
FIG. 7 is a schematic flow chart diagram illustrating one embodiment of yet another method for adjusting display settings of a head-mounted display.

FIG. 7 is a schematic flow chart diagram illustrating one embodiment of another method 700 for adjusting display settings of a head-mounted display. In one embodiment, the method 700 begins and checks 702 the sensors 106 to determine 704 whether the sensors 106 are responding, reading data, reading accurate data, and/or the like. If the method 700, in one embodiment, determines 704 that the sensors are not responding correctly, the method 700 notifies 706 the user to adjust the headband 104 and/or sensors 106.

In one embodiment, the method 700 receives 708 sensor data from the sensors 106 while the user wears the HMD unit 102. The method 700 may determine 710 whether this is the first time that the user has worn the HMD unit 102, if the user just activated the HMD unit 102, or the like. If so, then the method 700, in certain embodiments, generates 712 a baseline of sensor data for a period of time after the HMD unit 102 is activated prior to determining the user's visual acuity and adjusting the one or more display settings of the HMD unit 102.

If the method 700, in certain embodiments, determines 714 that the baseline data is sufficient, e.g., after a period of time, after the workload running on the HMD unit 102 and/or the sensor data has reached a steady state, after completing a calibration process, or the like, the method 700 determines 716 the user's visual acuity based on the sensor data, e.g., based on the theta- and alpha-wave frequency data and adjusts 718 the display settings of the HMD unit 102 accordingly. The method 700, in certain embodiments, continues to receive 708 sensor data, monitor the user's visual acuity, and adjust the display settings of the HMD unit 102. In some embodiments, the sensor module 202, the vision module 206, the adjustment module 208, the monitoring module 302, the notification module 304, and the baseline module 306 perform the various steps of the method 700.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
   a processor;
   a memory that stores code executable by the processor to:
      receive sensor data from one or more sensors operably connected to a head mounted display ("HMD") unit while a user wears the HMD unit;
      determine a user's cognition level based on the sensor data, the cognition level indicated by the sensor data relative to a threshold, the threshold comprising a value that is associated with a predefined cognition level;
      adjust one or more settings of a display of the HMD unit that has an effect on the user's cognition level based on the determined cognition level for the user;
      monitor, over time, the user's cognition level based on new sensor data from the one or more sensors while the user wears the HMD unit;
      further adjust the one or more display settings of the HMD unit based on the user's cognition level; and
      notify the user that the one or more sensors are not positioned in a correct location on the user's head in response to not receiving sensor data from one or more of the sensors.

2. The apparatus of claim 1, wherein the sensor data is sensed from one or more locations on the user's head, the one or more sensors coupled to a headband that is connected to the HMD unit.

3. The apparatus of claim 2, wherein the sensor data comprises electroencephalography ("EEG") data sensed from the one or more locations on the user's head.

4. The apparatus of claim 3, wherein the EEG data comprises a measurement of a signal strength that the one or more sensors sense within the beta-wave range, the user's cognition level determined according to the measured signal strength.

5. The apparatus of claim 2, wherein the one or more sensors comprise one or more electrode probes and the one or more locations on the user's head where the sensors are located is selected from the group consisting of FP1, FP2, TP9, and TP10 locations.

6. The apparatus of claim 1, wherein the code is further executable by the processor to generate a baseline of sensor data for a period of time after the HMD unit is activated prior to determining the user's cognition level and adjusting the one or more display settings of the HMD unit.

7. The apparatus of claim 1, wherein the code is further executable by the processor to acquire biometric data for the user, the biometric data further used to determine the user's cognition level.

8. The apparatus of claim 7, wherein the biometric data is selected from the group consisting of a skin conductivity for the user, a heart rate for the user, a blood pressure for the user, and an oxygen level for the user.

9. The apparatus of claim 1, wherein the code is executable by the processor to present one or more of an augmented reality ("AR") environment and a virtual reality ("VR") environment on a display of the HMD unit.

10. The apparatus of claim 9, wherein adjusting one or more settings of the HMD unit comprises changing one or more settings of the VR and AR environment, the one or more settings selected from the group consisting of a brightness setting of elements presented on the display, a contrast setting of the display between elements presented on the display and an actual background, a color of elements presented on the display, and a size of elements presented on the display.

11. A system, comprising:
    a head-mounted display ("HMD") unit comprising a processor and a memory that stores code executable by the processor;
    a headband coupled to the HMD unit; and
    one or more sensors coupled to the headband and operably connected to the HMD unit,
    wherein the code is executable by the processor to:
       receive sensor data from the one or more sensors while a user wears the HMD unit;
       determine a user's cognition level based on the sensor data, the cognition level indicated by the sensor data relative to a threshold, the threshold comprising a value that is associated with a predefined cognition level;
       adjust one or more settings of a display of the HMD unit that has an effect on the user's cognition level based on the determined cognition level for the user;
       monitor, over time, the user's cognition level based on new sensor data from the one or more sensors while the user wears the HMD unit;
       further adjust the one or more display settings of the HMD unit based on the user's cognition level; and
       notify the user that the one or more sensors are not positioned in a correct location on the user's head in response to not receiving sensor data from one or more of the sensors.

12. The system of claim 11, wherein the one or more sensors comprise one or more electrode probes positioned at one or more locations on the user's head, the one or more locations selected from the group consisting of TP9, FP1, FP2 and TP10 locations.

13. The system of claim 12, wherein the sensor data comprises electroencephalography ("EEG") data sensed from the one or more electrode probes located on the user's head.

14. The system of claim 11, wherein the code is executable by the processor to present one or more of an augmented reality ("AR") environment and a virtual reality ("VR") environment on a display of the HMD unit, the one or more settings of the VR and AR environment that are adjusted are selected from the group consisting of a brightness setting of elements presented on the display, a contrast setting of the display between elements presented on the display and an actual background, a color of elements presented on the display, and a size of elements presented on the display.

15. A method, comprising:
- receiving, by a processor, sensor data from one or more sensors operably connected to a head mounted display ("HMD") unit while a user wears the HMD unit;
- determining a user's cognition level based on the sensor data, the cognition level indicated by the sensor data relative to a threshold, the threshold comprising a value that is associated with a predefined cognition level;
- adjusting one or more settings of a display of the HMD unit that has an effect on the user's cognition level based on the determined cognition level for the user;
- monitoring, over time, the user's cognition level based on new sensor data from the one or more sensors while the user wears the HMD unit;
- further adjusting the one or more display settings of the HMD unit based on the user's cognition level; and
- notifying the user that the one or more sensors are not positioned in a correct location on the user's head in response to not receiving sensor data from one or more of the sensors.

16. The method of claim 15, further comprising generating a baseline of sensor data for a period of time after the HMD unit is activated prior to determining the user's cognition level and adjusting the one or more display settings of the HMD unit.

* * * * *